United States Patent [19]

Colle et al.

[11] Patent Number: 5,021,442
[45] Date of Patent: Jun. 4, 1991

[54] FUNGICIDE AZOLYL-DERIVATIVES

[75] Inventors: Roberto Colle, Basiglio; Giovanni Camaggi, Novara; Giuseppina Ratti, Seregno; Carlo Garavaglia, Cuggiono; Luigi Mirenna, Milan, all of Italy

[73] Assignee: Presidenza del Consiglio Dei Ministri, Rome, Italy

[21] Appl. No.: 267,317

[22] Filed: Nov. 4, 1988

[30] Foreign Application Priority Data

Nov. 9, 1987 [IT]  Italy ................ 22560 A/87

[51] Int. Cl.$^5$ ................ A01N 43/653; C07D 249/08
[52] U.S. Cl. ................ 514/383; 548/268.6; 548/267.8
[58] Field of Search ............ 514/383; 548/262, 267.8, 548/268.6

[56]     References Cited
       U.S. PATENT DOCUMENTS

| 4,382,944 | 5/1983 | Kramer et al. | 548/262 |
| 4,507,140 | 3/1985 | Sugavanam | 548/262 |
| 4,664,696 | 5/1987 | Schaub | 548/262 |

OTHER PUBLICATIONS

Montedison SPA, "Preparation of N-(2-Phenylethyl) etc.", CA 108:378436 (1988).
Schaper, "Azolylarylalkanol Derivatives, etc.", CA 104:5873n (1986).

Primary Examiner—Robert W. Ramsuer
Assistant Examiner—Patricia L. Morris
Attorney, Agent, or Firm—Morgan & Finnegan

[57] ABSTRACT

There are described compounds having general formula:

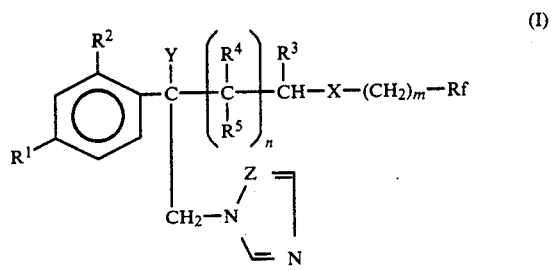

wherein:
$R^1$ is selected from the group comprising F, Cl, Br, $CF_3$, a phenyl, a $C_1$-$C_2$ alkoxy, a $C_1$-$C_2$ haloalkoxy, an alkylthio, a haloalkylthio radical, in which the halogen is F, Cl, Br;
$R^2$ is selected from the group comprising H, F, Cl, Br, $CF_3$;
$R^3$, $R^4$ and $R^5$, which may be the same or different, are H, a $C_1$-$C_4$ alkyl or a $C_3$-$C_6$ cycloalkyl radical, on condition that $R^5$ is different from $R^3$, when $R^4$ is H;
Y is selected from the group comprising H, $CH_3$, OH, CN, F;
n is 1,2;
m is 0,1;
X is O or S;
Rf is selected from the group consisting of $C_1$-$C_5$ polyfluoroalkyl, $C_2$-$C_4$ polyfluoroalkenyl, polyfluoroalkoxyalkyl and polyfluoroalkoxyalkenyl radicals, everyone of them containing at least two fluorine atoms and, optionally, other halogen atoms selected from Cl and Br;
Z is CH or N.

3 Claims, No Drawings

FUNGICIDE AZOLYL-DERIVATIVES

FIELD OF THE INVENTION

The present invention relates to azolyl-derivatives having immunizing activity against fungus pathogenesis and phytogrowth regulating activity towards useful growings, to the process for their preparation and to the corresponding employ of such compounds in agricultural field.

BACKGROUND OF THE INVENTION

From German patent 2.654,890 triazolylcarbinols are known, having general formula:

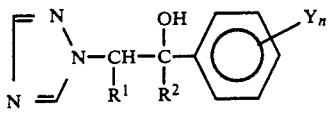

wherein: $R^1$ and $R^2$ are H or a hydrocarbyl group; with the expression hydrocarbyl a saturated or unsaturated, linear or branched chain or a single or condensed ring are meant and, when the hydrocarbyl group is or contains an aryl radical, this latter may be substituted; Y is, for instance, a halogen atom.

From European patent No. 150,036 azolyl-derivatives are also known, having formula:

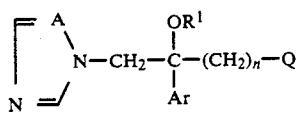

wherein Ar is a substituted aromatic group; A is CH, N; $n=2-12$; $R^1$=an alkyl, alkenyl, alkynyl or benzyl radical; $Q=S(O)_{1-2}-R^2$ or $OR^3$, in which $R^2$, $R^3$ are an alkyl, cycloalkyl, alkenyl or aryl radical independently.

Moreover from European patent application No. 145,294 compounds are known, having formula:

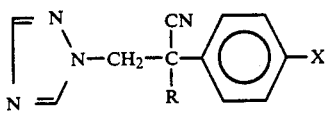

wherein R is a $C_3-C_8$ alkyl radical, on condition that, when R is a $C_3-C_6$ branched alkyl radical, the branch has not to be on carbon atom $\alpha$ of group R; X is a halogen atom.

We have now found a class of azolyl-derivatives, which differ from the ones of the prior art and are endowed with a higher immunizing activity against fungus pathogenesis and with phytogrowth regulating properties.

DETAILED DESCRIPTION OF THE INVENTION

Therefore an object of the present invention concerns the compounds having general formula:

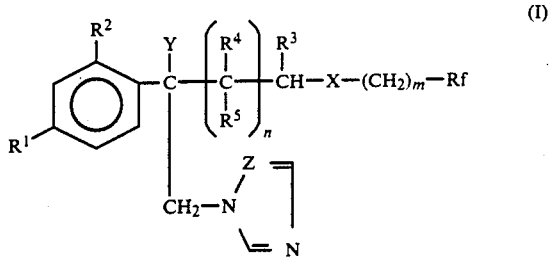

wherein:
$R^1$ is selected from the group comprising F, Cl, Br, $CF_3$, a phenyl, a $C_1-C_2$ alkoxy, a $C_1-C_2$ haloalkoxy, an alkylthio, a haloalkylthio radical, in which the halogen is F, Cl, Br;

$R^2$ is selected from the group comprising H, F, Cl, Br, $CF_3$;

$R^3$, $R^4$, $R^5$, which may be the same or different, are H, a $C_1-C_4$ alkyl or $C_3-C_6$ cycloalkyl radical, on condition that $R^5$ is different from $R^3$ when $R^4$ is H;

Y is selected from the group comprising H, $CH_3$, OH, CN, F;

n is 1,2;

m is 0,1;

X is O or S;

Rf is selected from the group consisting of $C_1-C_5$ polyfluoroalkyl, $C_2-C_4$ polyfluoroalkenyl, polyfluoroalkoxyalkyl and polyfluoroalkoxyalkenyl radicals, everyone of them containing at least two fluorine atoms and, optionally, other halogen atoms selected from Cl and Br;

Z is CH or N.

The compounds having general formula (I) are endowed, as above mentioned, with a higher immunizing activity against fungus pathogenesis and with phytogrowth regulating properties and may be employed advantageously in agricultural field.

The compounds of the present invention contain at least a kyral centre and are generally obtained in the form of racemic mixtures. The single enantiomers can be separated from these mixtures by methods, known in literature.

Both single enantiomers and possible diastereoisomers or geometric isomers, generated by several kyral centres or by possible double bonds, form an object of the present invention.

The following compounds form also an object of the present invention:
the salts of the compounds having general formula (I) coming from an inorganic acid such as a hydrohalogenic acid, for instance hydroiodic, hydrobromic, hydrochloric acid; sulphuric, nitric, thiocyanic and phosphoric acid; or from an organic acid such as acetic, propanoic, ethanedioic, propanedioic, benzoic, methanesulphonic, 4-methylbenzenesulphonic acid and the like;
the metal complexes obtained by complexation reaction between the derivatives of type (I) with an organic or inorganic metal salt such as halogenide, nitrate, sulphate, phosphate of, for instance, copper, manganese, zinc or iron.

The compounds having formula (I) of the present invention can be obtained by different processes according to the values of n, m and Y.

1) A general process for the preparation of the compounds having formula (I), when m is O, consists in carrying out an addition reaction of the compounds having formula:

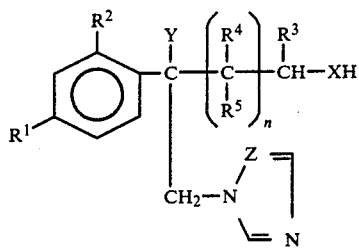

wherein $R^1$, $R^2$, $R^3$, $R^4$, $R^5$, X, Z and n have the meanings, as specified hereinbefore, to a fluoroolefin having formula:

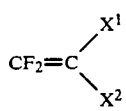

wherein $X^1$ is F, Cl, $CF_3$; $X^2$ is F, Cl, $CF_3$ or $-OX^3$, in which $X^3$ is a polyfluoroalkyl radical having from 1 to 3 carbon atoms, containing at least three fluorine atoms and optionally other halogen atoms selected from Cl and Br, in the presence of aprotic solvents, such as, for instance, DMF, DMSO, THF, dioxane or pyridine, or in an alcoholic solvent, such as, for instance terbutanol, in the presence of catalytic or stoichiometric amounts of a strong organic or inorganic base, such as, for instance, sodium hydride, potassium terbutilate and potassium hydroxide, at temperatures ranging from $-20°$ C. to $100°$ C., to yield the compounds having formula;

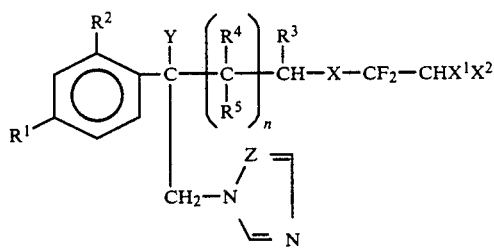

By subsequent dehydrofluorination reaction of the compounds of formula (Ia), which reaction may also take place spontaneously during the above described reaction, an unsaturation may be introduced in the α-position of group Rf, thereby obtaining the unsaturated compounds having formula:

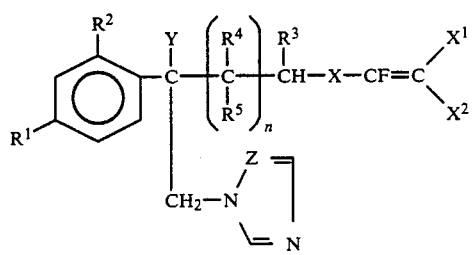

2) Another process for the preparation of the compounds having formula (I), when X is O and m is 1, consists in carrying out a reaction of nucleophil substitution on the reactive ester having formula:

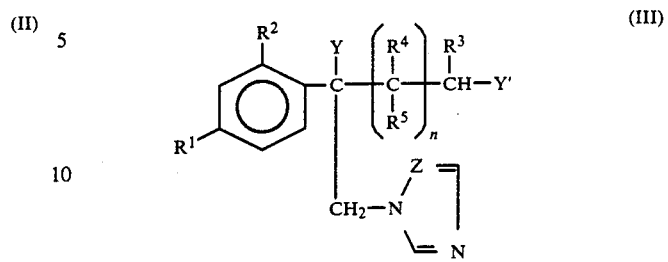

wherein Y' represents a halogen atom or a mesyl or tosyl group, by means of an alkaline salt of a polyfluorinated alcohol of formula (IV), according to the reaction scheme:

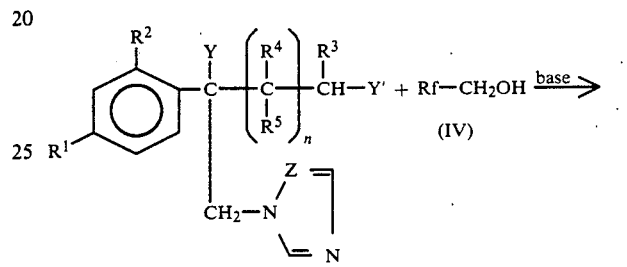

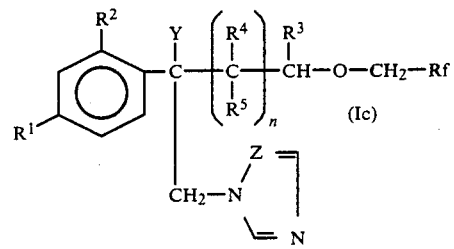

The reaction is carried out preferably in aprotic dipolar solvents, such as DMF, DMSO or ethereal solvents, such as, for instance, diethylether, THF or dioxane, in the presence of stoichiometric amounts of a strong base, such as, for instance, sodium hydride or potassium terbutylate. The reactive ester of formula (III) can be obtained easily, by treating the corresponding primary alcohol of formula (II), wherein X is O, with a halogenation, tosylation or mesylation agent.

3) Another process for the preparation of the compounds having formula (I), when m is 0, consists in letting react an alkaline salt of a compound of formula (II) with a polyfluoro-alkyl-halogenide having formula: Rf-$X^4$, in which $X^4$ is a halogen atom, such as chlorine, bromine or fluorine, according to the reaction scheme:

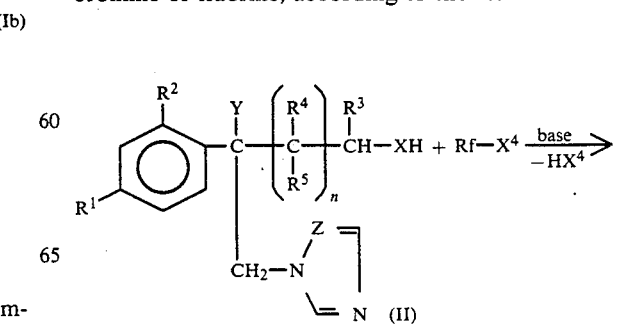

-continued

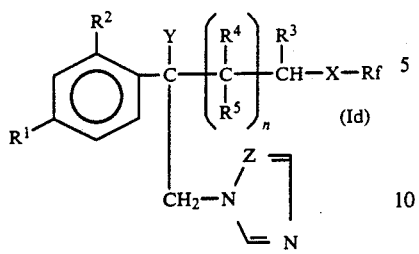
(Id)

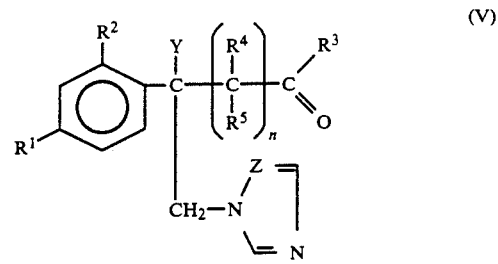
(V)

the reaction is carried out under conditions similar to the ones indicated hereinbefore for process 2).

4) Another process for the preparation of the compounds having formula (I), when Y is —OH, consists in letting react a polyfluorinated oxirane of formula (IX) with an alkaline salt of an azole, according to the reaction scheme:

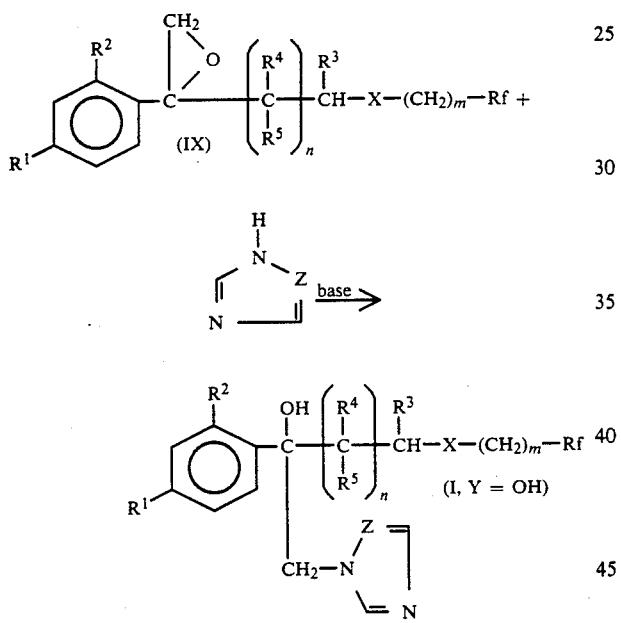

The reaction is generally carried out in an aprotic dipolar solvent, such as DMSO o DMF, in the presence of stoichiometric amounts of a strong base, such as sodium hydride, potassium terbutylate or KOH, at temperatures ranging from the room temperature to the reflux temperature of the solvent.

5) Another process for the preparation of the compounds having formula (I) when Y is F, consists in treating the compounds of formula (I), in which Y=OH, with diethylaminosulphotrifluoro (DAST) in an inert solvent, such as, for instance, methylene chloride, at temperatures ranging from −70° to 0° C.

The intermediate compounds of formula (II), when X is O, employed in processes 1) and 3), may be prepared by reduction of the carbonylic compounds having formula:

wherein $R^1$, $R^2$, $R^3$, $R^4$, $R^5$, n, Y and Z have the meanings, as specified hereinbefore. The reduction of the compounds having formula (V) can be carried out, by using mixed hydrides, such as, for instance, $LiAlH_4$, $LiBH_4$, $NaBH_4$, in solvents of ethereal kind, such as, for instance, diethylether, THF, at temperatures ranging from 0° C. to 30° C. The intermediate compounds of formula (V) can, in their turn, be prepared by different methods, according to the nature of Y and the value of n.

a) When Y=OH the intermediate compounds of formula (V) can be prepared starting from the compounds having formula (VI), according the reaction schemes:

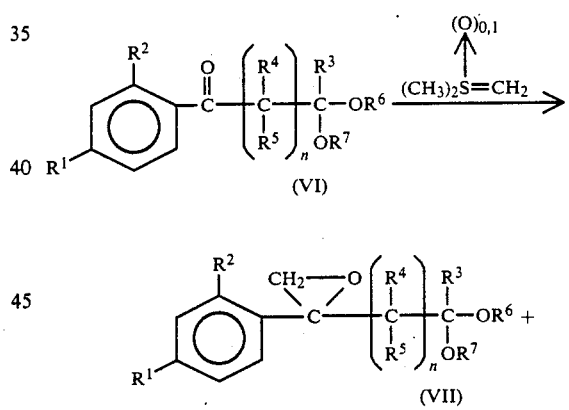

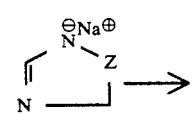

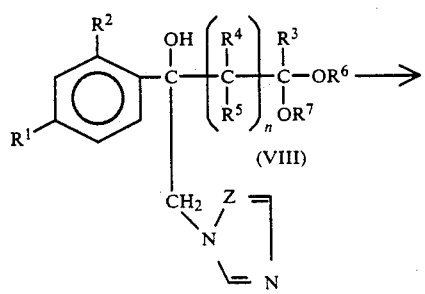

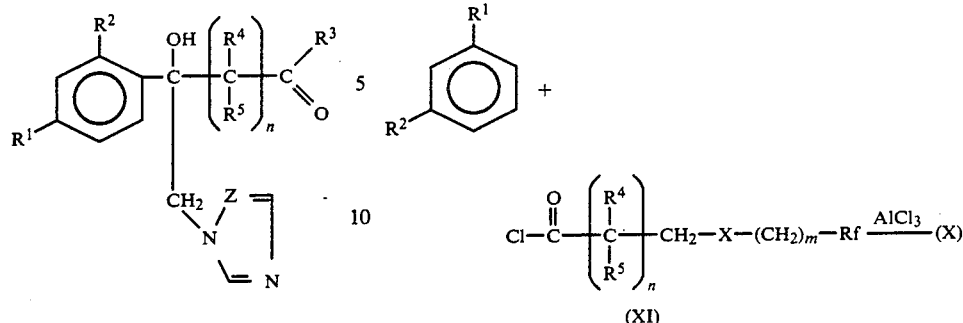

wherein $R^6$, $R^7$ are —$CH_3$ or form together a —$CH_2$—$CH_2$ group. The compounds having formula (VI) are known for instance, from: Panizzi, Gazz. Chim. Ital. 77, 549 (1947); Furuya et.al, Chem. Pharm. Bull. 1982, 30 (7), 2424.

The conversion reaction of compounds (VI) into oxiranes (VII) is carried out according to a known method, for instance from: Corey, Chaykovsky, J.A.C.S. 87 (1965) 1353 and J.A.C.S. 84 (1962)3782.

The conversion of oxiranes (VII) into carbinols (VIII), is carried out by reaction of an azole with an alkaline salt, in an aprotic dipolar solvent, such as, for instance, DMSO or DMF, in the presence of stoichiometric amounts of a strong base, such as sodium hydride, potassium terbutylate or potassium hydroxide, at temperatures ranging from the room temperature and the reflux temperature of the solvent.

Finally the hydrolysis reaction of compounds (VIII) is generally carried out in an alcoholic solvent, such as ethanol or methanol, in the presence of a mineral acid, such as hydrochloric or sulphuric acid, at temperatures ranging from 0° C. to the boiling point of the solvent.

b) When Y is different from OH, the intermediate compounds of formula (V) can be prepared by known methods, for instance, when Y=H, they can be obtained by dehydration of the compounds having formula (V), in which Y=OH, and subsequent catalytic hydrogenation of the resultant olefin.

The intermediate oxiranes of formula (IX), when $R^3$ is H, employed in process 4) can be prepared by letting react ketones (X) with a sulfonium hylide or sulfoxonium hylide, by using a method known, for instance, from Corey, Chaykovsky, J.A.C.S. 87 (1965)1353 and J.A.C.S. 84 (1962) 3782, according to the reaction scheme:

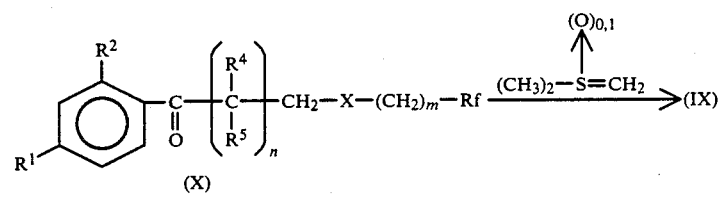

The ketones of formula (X) can, in their turn, be prepared by Friedel-Kraft condensation, starting from acid chlorides of formula (XI), according to the following reaction:

This reaction, already known, is carried out by using as solvent the same benzenic derivative, used as starting compound at temperatures ranging from the room temperature to the boiling temperature of the mixture.

For the synthesis of the acid chlorides having formula (XI), it is convenient to start from a ω-hydroxy (or mercapto) ester of formula (XII), in which R is an ethyl or methyl radical, afterwards, by following the above described reaction schemes, concerning methods 1), 2) and 3) for the preparation of the compounds of formula (I), fluorinated esters (XIII) are obtained.

The esters of formula (XIII), thus obtained, are then hydrolyzed, in an alkaline aqueous medium, to yield the corresponding acids (XIV), that, in their turn, are converted into the acid chlorides of formula (XI), by means of a chlorination agent, for instance thionyl chloride, optionally in the presence of a catalyst, such as DMF, at temperatures ranging from 20° to 60° C., according to the reaction schemes:

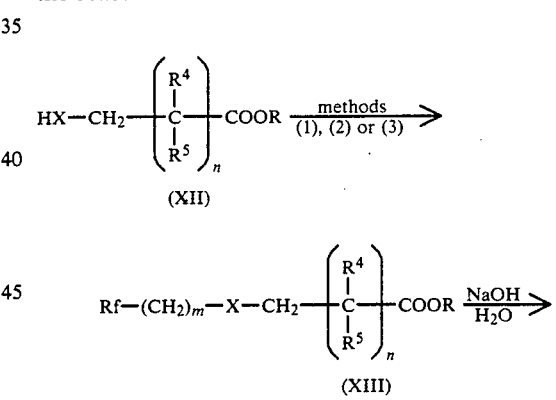

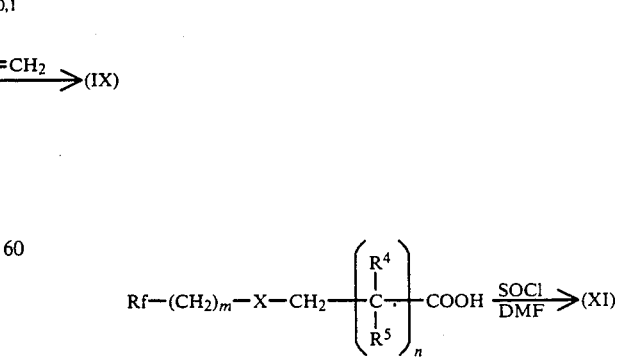

In particular, the compounds of formula (XIII), when m=0 and Rf=$X^1X^2CH$—$CF_2$—, in which $X^1$ and $X^2$ have the meanings, as specified hereinbefore, are prepared by letting react esters (XII) with a fluoroolefin having formula: $CF_2=CX^1X^2$, in the presence of aprotic solvents, such as for instance, DMF, DMSO, THF, dioxane or pyridine, or in an alcoholic solvent, such as for instance terbutanol, in the presence of catalytic or stoichiometric amounts of a strong organic or inorganic base, such as, for instance, sodium hydride, potassium terbutylate, at temperatures ranging from $-20°$ C. to $100°$ C., according to the reaction scheme:

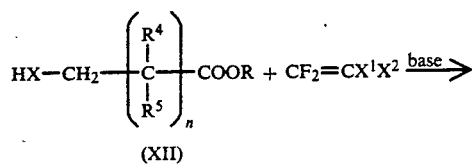

(XII)

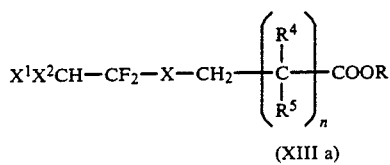

(XIII a)

Examples of compounds having general formula (I), according to the present invention, are set forth in Table 1.

*Piricularia oryzae* on rice
*Botrytis cinerea*
Fusarium on cereals and still other deseases.

The compounds of formula (I) are endowed with immunizing action having both curative and preventive character, show a complete compatibility towards the plants, which have to be protected, moreover these compounds are characterized by systemic properties.

These properties allow the products to enter the vascular systems of the plants and to act even in sites (for instance leaves), that are very far away from the ones they have been applied in (for instance, roots).

For the practical uses in agriculture it is often advantageous to make use of fungicide compositions containing one or more compounds of formula (I) as active substance.

The application of these compositions can take place on every part of the plant, for instance, leaves, stalks, branches and roots or on the seeds themselves, before the sowing, or on the soil adjoning the plant as well. The compostions may be used, in the form of dry powders, wettable powders, emulsifiable concentrates, pastes, granulates, solutions, suspensions and the like: the choice of the kind of composition will depend on the specific use. The compositions are prepared, according to a known way, for instance, by diluting or dissolving the active substance by means of a solvent medium and/or a solid diluent, optionally in the presence of surfactants. The following compounds may be

TABLE 1

(I)

[Structure showing benzene ring with substituents $R^1$, $R^2$, $CH_2-N$ connected to Z=N/N ring, and chain $-C(Y)-(C(R^4)(R^5))_n-CH(R^3)-X-(CH_2)_m-Rf$]

| COMPOUND No | Y | $R^1$ | $R^2$ | $R^3$ | $R^4$ | $R^5$ | Z | X | m | n | Rf |
|---|---|---|---|---|---|---|---|---|---|---|---|
| 1 | —OH | Cl | H | H | H | $CH_3$ | N | O | 0 | 1 | $-CF_2-CF_2H$ |
| 2 | —OH | Cl | Cl | H | H | $CH_3$ | N | O | 0 | 1 | $-CF_2-CF_2H$ |
| 3 | —OH | Cl | Cl | $C_2H_5$ | H | $CH_3$ | N | O | 0 | 1 | $-CF_2-CF_2H$ |
| 4 | —OH | Cl | H | H | $CH_3$ | $CH_3$ | N | O | 0 | 1 | $-CF_2-CF_2H$ |

The compounds having general formula (I) are endowed with immunizing activity against fungus pathogenesis and with phytogrowth regulating activity and may be used advantageously in agricultural field.

Their fungicide activity proves to be particularly high against phytopathogenous fungi infesting cereal cultivations, fruit-growing, industrial and horticultural cultivations.

Examples of plant diseases that can be fought by using the compounds of the present inventions are the following ones:
*Erysiphe graminis* on cereals
*Sphaeroteca fuliginea* on cucurbitaceae (for inst.cucumber)
Puccinia on cereals
Septoria on cereals
Helminthosporium on cereals
Rhynchosporium on cereals
*Podosphaera leucotricha* on apple-trees
*Uncinula necator* on vines
*Venturia inaequalis* on apple-trees used as solid diluents or carriers: silica, kaolin, bentonite, talc, diatomite, dolomite, calcium carbonate, magnesia, gypsum, clays, synthetic silicates, attapulgite, sepiolite. Besides of course, water, several kinds of solvents may be used as liquid diluents, for instance, aromatic solvents (benzene, xylenes, or mixtures of alkylbenzenes), chloroaromatic solvents (chlorobenzene), paraffins (oil cuts), alcohols (methanol, propanol, butanol), amines, amides (dimethylformamide), ketones (cyclohexanone, acetophenone, isophorone, ethyl-amyl-ketone), esters (isobutylacetate). As surfactants: sodium salts, calcium salts or triethanolamine of alkylsulfates, alkylsulfonates, alkyl-aryl-sulfonates, polyethoxylated alkylphenols, fatty alcohols condensed with ethylene oxide, polyoxyethylated fatty acids, polyoxyethylated sorbitol esters, polyoxyethylated fats, ligninsulfonates. The compositions may also contain special additives for particular purposes, for instance adhesives such as gum-arabic, polyvinyl alcohol, polyvinylpyrrolidone.

If desired, other compatible active substances may be also added to the compositions, object of the present invention, such as fungicides, phytodrugs, phytogrowth regulators, herbicides, insecticides, fertilizers.

The concentration of active substance in aforesaid compositions can vary within a wide range, according to the active compound, the cultivation, the pathogen, environmental conditions and the kind of formulation, that has been used. The concentration of active substance generally ranges from 0.1 to 95, preferably from 0.5 to 90% by weight.

EXAMPLE

The invention will now be illustrated by the following examples.

EXAMPLE 1

Preparation of 1-(1,2,4-triazolyl)-2-hydroxy-2-(4-chlorophenyl)-3-methyl-4-(1,1,2,2-tetrafluoroethoxy)butane (compound No 1)

Potassium terbutylate (0.1 g) was added to 1-(1,2,4-triazolyl)-2-(4-chlorophenyl)-2,4-dihydroxy-3-methyl-butane (1 g) dissolved in anhydrous THF (5 ml), anhydrous DMSO (10 ml), anhydrous terbutanol (10 ml), under nitrogen atmosphere, at $-10°$ C.

After having produced the vacuum in the apparatus, tetrafluoroethylene was introduced there and the whole was kept under atmosphere of this gas over 20 hours, at room temperature.

Then the reaction mixture was poured into water and extracted by means of methylene chloride.

The extract was rinsed with water, dried on anhydrous sodium sulfate and evaporated. The crude product thus obtained, was analyzed by silica gel chromatography, by eluting with 7:3, then 1:1 n-hexane-ethyl acetate.

0.2 g of a whitish oil were isolated, which was characterized as being in keeping with the structure indicated in the title, on the ground of the following spectroscopic data.

I.R. ($\nu$, cm$^{-1}$) 3300, 1280, 1120,

N.M.R. $^1$H (60 MHz) TMS in CDCl$_3$, $\delta$ : 0.90 (d, 3H); 2.80–3.10 (m, 1H); 3.20–3.80 (m, 2H); 4.40 (d, 1H); 5.10 (s, 1H); 5.30 (d, 1H); 5.60 (tt, 1H); 6.90–7.30 (m, 4H); 7.50–7.90 (m, 2H).

EXAMPLES 2–4

By following the method described in example 1, one prepared compounds No. 2,3,4 of Table 1, whose spectroscopic data are set forth hereinafter.

Compound No. 2

1-(1,2,4-triazolyl)-2-hydroxy-2-(2,4-dichlorophenyl)-3-methyl-4-(1,1,2,2-tetrafluoroethoxy)-butane I.R. $\nu$ cm, 3300, 1220, 1120, 1060, 1030.

N.M.R. $^1$H (60 MHz), TMS in CDCl$_3$$\delta$ : 0.60 (d, 3H); 2.80–3.20 (m, 1H); 3.80–4.50 (m, 2H); 4.55 (d, 1H); 4.65 (s, 1H); 5.35 (d, 1H); 5.60 (tt, 1H); 6.80–7.40 (m, 3H); 7.55 (s, 1H); 7.65 (s, 1H).

Compound No. 3

1-(1,2,4-triazolyl)-2-hydroxy-2-(2,4-dichlorophenyl)-3-methyl-4-(1,1,2,2-tetrafluoroethoxy)-hexane I.R. $\nu$ cm, 3400, 1280, 1220, 1120.

N.M.R. $^1$H (60 MHz), TMS in CDCl$_3$, $\delta$ : 0.75 (d, 3H); 1.00 (t, 3H); 2.05 (q, 2H); 2.90–3.40 (m, 1H); 4.30–4.70 (m, 1H); 4.75 (d, 1H); 5.30 (s, 1H); 5.65 (d, 1H); 5.75 (tt, 1H); 7.00–7.65 (m, 3H); 7.75 (s, 1H); 7.95 (s, 1H).

Compound No. 4

1-(1,2,4-triazolyl)-2-hydroxy-2-(4-chlorophenyl)-3-3-dimethyl-4-(1,1,2,2-tetrafluoroethoxy)-butane I.R. $\nu$ cm, 3120, 3100, 1120, 1100.

N.M.R. $^1$H (60 MHz), TMS in CDCl$_3$, $\delta$ : 1.05 (s, 3H); 1.10 (s, 3H); 3.70 (d, 1H); 4.15 (d, 1H); 4.55 (d, 1H); 4.90 (s, 1H); 5.10 (d, 1H); 5.75 (tt, 1H); 7.10–7.55 (m, 4H); 7.70 (s, 1H); 7.90 (s, 1H).

EXAMPLE 5

Determination of the immunizing activity against cucumber oidium (*Sphaerotheca fuliginea* (Schlech) Salmon).

Preventive activity:

Cucumber plants c.v. Marketer, grown in pots in a conditioned environment, were sprayed on their lower leaf faces with the products being tested in a water-acetone solution, containing 20% of acetone (vol.vol.). Then the plants were kept in a conditioned environment for 1 day, afterwards they were sprayed on their upper leaf faces with an aqueous suspension of conidia of *Sphaerotheca fuliginea* (200.000 conidia/ml). The plants were then carried back to a conditioned environment.

At the end of the incubation period of the fungus (8 days) the infection degree was valued according to indexes of a valuation scale ranging from 100 (=sound plant) to 0 (=completely infected plant).

Curative activity:

Cucumber plants cv. Marketer, grown in pots in a conditioned environment, were sprayed on their upper leaf faces with an aqueous suspension of conidia of *Sphaerotheca fuliginea* (200.000 conidia/ml.). 24 hours after the infection the plants were treated with the products being tested in a water-acetone solution containing 20% of acetone (vol/vol.) by spraying both leaf faces.

At the end of the incubation period of the fungus (8 days), during which time the plants were kept a suitably conditioned environment, the infection degree was valued according to indexes of a valuation scale ranging from 100 (=sound plant) to 0 (=completely infected plant).

The results are set forth in Table 2.

EXAMPLE 6

Determination of the immunizing activity against wheat oidium (*Erysiphe graminis* D.C.)

Preventive activity:

Leaves of wheat cv. Irnerio, grown in pots in a conditioned environment, were treated, by spraying both leaf faces with the products being tested, in a water-acetone solution containing 20% of acetone (vol./vol.).

After a stay time of 1 day in a conditioned environment at 20° C. and 70% of relative humidity, the plants were sprayed on both leaf faces with an aqueous suspension of *Erysiphe graminis* (200.000 conidia/cc.). After a stay time of 24 hours in an environment saturated with moisture, at 21° C., the plants were kept in a conditioned environment for fungus incubation.

At the end of said period of time (12 days), the infection degree was valued according to indexes of a scale ranging from 100 (sound plant) to 0 (completely infected plant).

Curative activity:

Leaves of wheat cv. Irnerio, grown in pots in a conditioned environment, were sprayed on both leaf faces with an aqueous suspension of *Erysiphe graminis* (200.000 conidia/cc). After a stay time of 24 hours in an environment saturated with moisture, at 21° C., the leaves were treated with the products being tested, in a water-acetone solution containing 20% of acetone (vol/vol), by spraying both leaf faces.

At the end of the incubation period (12days), the infection degree was valued at sight, according to indexes of a valuation scale ranging from 100 (=sound plant) to 0 (=completely infected plant).

The results are set forth in Table 2.

EXAMPLE 7

Determination of the immunizing activity against wheat linear rust (*Puccinia graminis* Pers.)

Preventive activity:

Leaves of wheat cv. Irnerio, grown in pots in a conditioned environment, were treated by spraying both leaf faces with the products being tested in an aqueous water-acetone solution containing 20% of acetone (vol/vol). After a stay time of 1 day in a conditioned environment, at 23° C. and 70% of relative humidity, the plants were sprayed on both leaf faces with a mixture of spores of *Puccinia graminis* in talc (100 mg of spores/5 g of talc).

After a stay time of 48 hours in an environment saturated with moisture, at 21° C., the plants were kept in a conditioned environment for fungus incubation.

At the end of said period of time (14 days), the infection degree was valued at sight, according to indexes of a scale ranging from 100 (sound plant) to 0 (completely infected plant).

Curative activity:

Leaves of wheat cv. Irnerio, grown in pots in a conditioned environment, were sprayed on both leaf faces with a mixture of spores of *Puccinia graminis* in talc (100 mg of spores/5 g of talc); after a stay time of 48 hours in an environment saturated with moisture, at 21° C., the leaves were treated with the products being tested in a water-acetone solution containing 20% of acetone (vol/vol), by spraying both leaf faces.

At the end of the incubation period (14 days) the infection degree was valued at sight, according to indexes of a valuation scale ranging from 100 (=sound plant) to 0 (completely infected plant).

The results are set forth in Table 2.

EXAMPLE 8

Determination of the fungicide activity against apple-tree Ticchiolatura (*Venturia inaequalis* (CKe) Wint)

Preventive activity:

Leaves of apple-trees cv. Starking, grown in pots in a glasshouse, were treated by spraying both leaf faces with the products being tested, in a water-acetone solution containing 20% of acetone (vol/vol). After a stay time of 1 day in a conditioned environment, at 20° C. and 70% of relative humidity, the plants were sprayed uniformly with an aqueous suspension of conidia of *Venturia inaequalis* (200.000 conidia/cc). After a stay time of 2 days in an environment saturated with moisture, at 21° C., the plants were kept in a conditioned environment for fungus incubation.

At the end of this period (14 days) the infection degree was valued at sight, according to indexes of a valuation scale ranging from 100 (sound plant) to 0 (completely infected plant).

Curative activity:

Leaves of apple-trees cv. Starking, grown in pots in a glasshouse, were sprayed uniformly with an aqueous suspension of conidia of *Venturia inaequalis* (200.000 conidia/cc); after a stay time of 2 days in an environment saturated with moisture, said leaves were treated with the products being tested, in a water-acetone solution containing 20% of acetone (vol/vol), by spraying both leaf faces. At the end of the incubation period (14 days) the infection degree was valued at sight, according to indexes of a valuation scale ranging from 100 (sound plant) to 0 (completely infected plant).

The results are set forth in Table 2.

TABLE 2

| COMPOUND No | DOSE g/l | *Sphaeroteca fuliginea* cucumber | | *Erysiphe graminis* wheat | | *Puccinia graminis* wheat | | *Venturia inaequalis* apple-tree | |
|---|---|---|---|---|---|---|---|---|---|
| | | Preventive activity | Curative activity | Preventive activity | Curative activity | Preventive activity | Curative activity | Preventive activity | Curative activity |
| 1 | 0.5 | 100 | 100 | 100 | 100 | 100 | 100 | 100 | 100 |
| | 0.25 | 100 | 100 | 100 | 100 | 100 | 100 | 100 | 100 |
| | 0.125 | 100 | 100 | 100 | 100 | 100 | 100 | 100 | 100 |
| 2 | 0.5 | 100 | 100 | 100 | 100 | 100 | 100 | 100 | 100 |
| | 0.25 | 100 | 100 | 100 | 100 | 100 | 100 | 100 | 100 |
| | 0.125 | 100 | 100 | 100 | 100 | 100 | 100 | 100 | 100 |
| 3 | 0.5 | 100 | 100 | 100 | 100 | 100 | 100 | 100 | 100 |
| | 0.25 | 100 | 100 | 100 | 100 | 100 | 100 | 100 | 100 |
| | 0.125 | 100 | 100 | 100 | 100 | 100 | 100 | 100 | 100 |
| 4 | 0.5 | 100 | 100 | 100 | 100 | 100 | 100 | 100 | 100 |
| | 0.25 | 100 | 100 | 100 | 100 | 100 | 100 | 100 | 100 |
| | 0.125 | 100 | 100 | 100 | 100 | 100 | 100 | 100 | 100 |

What we claim is:

1. 1-(1,2,4-triazolyl)-2-hydroxy-2-(2,4-dichlorophenyl)-3-methyl-4-(1,1,2,2-tetrafluoroethoxy)butane.

2. Fungicide composition having as active ingredient an effective amount of 1-(1,2,4-triazolyl)-2-hydroxy-2-(2,4-dichlorophenyl)-3-methyl-4-(1,1,2,2,-tetrafluoroethoxy) butane, together with an inert solid or liquid carrier.

3. A method of controlling fungus infections in useful plants consisting in distributing on the plant, on the seeds or in the area adjoining the plant, when the fungus infection is foreseen or it is already in progress, an effective amount of 1-(1,2,4-triazolyl)-2-hydroxy-2-hydroxy-2-(2,4-dichlorophenyl)-3-methyl-4-(1,1,2,2,-tetrafluoroethoxy) butane, either as such or in the form of a suitable composition.

* * * * *